US012004773B2

(12) United States Patent
Meglan

(10) Patent No.: US 12,004,773 B2
(45) Date of Patent: Jun. 11, 2024

(54) SENSORIZING ROBOTIC SURGICAL SYSTEM ACCESS PORTS

(71) Applicant: Covidien LP, Mansfield, MA (US)

(72) Inventor: Dwight Meglan, Westwood, MA (US)

(73) Assignee: COVIDIEN LP, Mansfield, MA (US)

( * ) Notice: Subject to any disclaimer, the term of this patent is extended or adjusted under 35 U.S.C. 154(b) by 793 days.

(21) Appl. No.: 17/024,900

(22) Filed: Sep. 18, 2020

(65) Prior Publication Data

US 2021/0000503 A1 Jan. 7, 2021

Related U.S. Application Data

(62) Division of application No. 15/521,015, filed as application No. PCT/US2015/055456 on Oct. 14, 2015, now Pat. No. 10,779,856.

(Continued)

(51) Int. Cl.
*A61B 17/34* (2006.01)
*A61B 34/00* (2016.01)
(Continued)

(52) U.S. Cl.
CPC .......... *A61B 17/3423* (2013.01); *A61B 34/30* (2016.02); *A61B 34/35* (2016.02);
(Continued)

(58) Field of Classification Search
CPC ..... A61B 17/3423; A61B 34/30; A61B 34/35; A61B 34/76; A61B 2034/302;
(Continued)

(56) References Cited

U.S. PATENT DOCUMENTS

| 5,449,370 A | 9/1995 | Vaitekunas |
| 6,010,461 A | 1/2000 | Haniff et al. |

(Continued)

FOREIGN PATENT DOCUMENTS

| JP | 2002159509 A | 6/2002 |
| JP | 2004288486 A | 10/2004 |

OTHER PUBLICATIONS

Extended European Search Report corresponding to counterpart Patent Appln. EP 15 85 3267.1 dated May 8, 2018.

(Continued)

*Primary Examiner* — Richard G Louis
(74) *Attorney, Agent, or Firm* — Carter, DeLuca & Farrell, LLP

(57) ABSTRACT

A robotic surgical system includes an access port having a plurality of sensors incorporated therein and a surgical instrument having an end effector for use with, and connection to a robot arm. The sensors measure a loading parameter between tissue and the access port when the shaft is inserted through the access port. The sensors wirelessly transmit signals indicative of the loading parameter to a processing unit. The estimated loads at the tip of the end effector of the surgical instrument are provided in real-time to a haptic feedback interface for communicating haptic feedback to a user. The haptic feedback increases or decreases in intensity in response to a specific event, occurrence, or operational characteristic related to the estimated loads.

14 Claims, 5 Drawing Sheets

Related U.S. Application Data

(60) Provisional application No. 62/068,040, filed on Oct. 24, 2014.

(51) Int. Cl.
*A61B 34/30* (2016.01)
*A61B 34/35* (2016.01)
*A61B 90/00* (2016.01)

(52) U.S. Cl.
CPC ........ *A61B 34/76* (2016.02); *A61B 2034/302* (2016.02); *A61B 2090/064* (2016.02); *A61B 2090/065* (2016.02); *A61B 2090/0811* (2016.02)

(58) Field of Classification Search
CPC ........ A61B 2090/064; A61B 2090/065; A61B 2090/0811; A61B 17/00234
See application file for complete search history.

(56) References Cited

U.S. PATENT DOCUMENTS

| | | | |
|---|---|---|---|
| 6,387,043 B1 | 5/2002 | Yoon | |
| 6,527,704 B1 | 3/2003 | Chang et al. | |
| 7,927,272 B2 | 4/2011 | Bayer et al. | |
| 7,981,092 B2 | 7/2011 | Duke | |
| 8,004,229 B2 | 8/2011 | Nowlin et al. | |
| 8,439,830 B2 | 5/2013 | McKinley et al. | |
| 8,523,043 B2 | 9/2013 | Ullrich et al. | |
| 8,535,270 B2 | 9/2013 | Davis et al. | |
| 8,550,981 B2 | 10/2013 | Woodruff et al. | |
| 8,591,470 B2 | 11/2013 | Rockrohr | |
| 8,840,628 B2 | 9/2014 | Green et al. | |
| 9,198,714 B2 | 12/2015 | Worrell et al. | |
| 10,779,856 B2 | 9/2020 | Meglan | |
| 2007/0013336 A1 | 1/2007 | Nowlin et al. | |
| 2007/0021742 A1* | 1/2007 | Viswanathan | A61B 18/04 606/1 |
| 2007/0244488 A1* | 10/2007 | Metzger | A61B 17/025 606/90 |
| 2008/0140088 A1 | 6/2008 | Orban, III | |
| 2009/0192523 A1* | 7/2009 | Larkin | A61B 34/20 606/130 |
| 2011/0046637 A1 | 2/2011 | Patel et al. | |
| 2011/0178477 A1 | 7/2011 | Morel et al. | |
| 2012/0197078 A1 | 8/2012 | Stanley | |
| 2013/0041288 A1* | 2/2013 | Taylor | A61B 5/6878 600/587 |
| 2013/0096501 A1 | 4/2013 | Arne et al. | |
| 2013/0150865 A1* | 6/2013 | Min | A61B 17/3421 606/130 |
| 2013/0172908 A1 | 7/2013 | Sang et al. | |
| 2013/0338480 A1 | 12/2013 | Hann | |
| 2014/0005682 A1 | 1/2014 | Worrell et al. | |
| 2014/0236177 A1 | 8/2014 | Verner et al. | |

OTHER PUBLICATIONS

Chinese First Office Action corresponding to counterpart Patent Appln. CN 201580057393.2 dated Dec. 3, 2018.
International Search Report for (PCT/US2015/055456) date of completion is Feb. 29, 2016 (4 pages).
Japanese Office Action dated May 30, 2019 corresponding to counterpart Patent Application JP 2017-521993.
Chinese Office Action for application No. 201580057393.2 dated Aug. 6, 2019 with English translation.

* cited by examiner

SENSORIZING ROBOTIC SURGICAL SYSTEM ACCESS PORTS

CROSS-REFERENCE TO RELATED APPLICATIONS

This application is a Divisional of U.S. patent application Ser. No. 15/521,015, filed on Apr. 21, 2017, which is a U.S. National Stage Application filed under 35 U.S.C. § 371(a) of International Patent Application Serial No. PCT/US2015/055456, filed Oct. 14, 2015, which claims the benefit of and priority to U.S. Provisional Patent Application Ser. No. 62/068,040, filed Oct. 24, 2014, the entire disclosure of which is incorporated by reference herein.

BACKGROUND

Robotic surgical systems have been used in minimally invasive medical procedures. Some robotic surgical systems include a console supporting a robot arm, and at least one surgical instrument, such as forceps or a grasping tool including jaws for capturing tissue therebetween. The at least one surgical instrument is mounted to the robot arm. During a medical procedure, the surgical instrument is inserted into a small incision (e.g., via a cannula) or a natural orifice of a patient to position the surgical instrument at a work site within the body of the patient.

Prior to or during use of the robotic surgical system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit drives the actuation of the surgical instrument. The tip of the surgical instrument experiences forces and torques when the surgical instrument is driven by the drive unit.

Traditional robotic surgical systems measure the forces and torques on a tip of a surgical instrument held by the robot arm (or robot end effector) by placing sensors at the tip of the surgical instrument. This methodology requires modifying the surgical instrument to incorporate the sensors in the surgical instrument, and in particular, near the tip of the surgical instrument by running wiring through the surgical instrument and out through some form of connector. This methodology adds complexity and cost to the surgical instrument.

Therefore, there is a need for sensing or determining conditions at a tip of a surgical instrument without placing sensors directly on the tip of the surgical instrument.

SUMMARY

According to an aspect of the present disclosure, a robotic surgical system is provided. The robotic surgical system includes an access port including a plurality of first sensors incorporated therein, the access port secured within tissue and a surgical instrument having an end effector for use with, and connection to a robot arm of the robotic surgical system, the surgical instrument including at least a shaft. The first sensors are configured to measure at least one loading parameter between tissue and the access port when the shaft is inserted through the access port.

In some embodiments, the first sensors transmit signals indicative of the at least one loading parameter to a processing unit of the robotic surgical system. The transmission of the signals may occur wirelessly or through wires and the transmission may occur continuously and in real-time.

In aspects of the present disclosure, the at least one loading parameter is related to at least one of a force or a torque applied at a tip of the end effector of the surgical instrument.

In another aspect of the present disclosure, the robotic surgical system includes a plurality of second sensors for measuring at least one of a force or a torque on the surgical instrument attached to the robot arm of the robotic surgical system. Measurements received from the plurality of first and second sensors are combined to estimate loads at a tip of the end effector of the surgical instrument.

In some instances, the estimated loads at the tip of the end effector of the surgical instrument are provided in real-time to a haptic feedback interface for communicating haptic feedback to a user. The haptic feedback increases or decreases in intensity in response to a specific event, occurrence, or operational characteristic related to the estimated loads.

In some embodiments, the end effector is controlled and/or articulated by at least one motor of a control device of the robotic surgical system, the at least one motor configured to receive the signals from the plurality of first and second sensors to, continuously and in real-time, adjust loads applied at the tip of the end effector of the surgical instrument.

According to another aspect of the present disclosure, a surgical access port is provided. The surgical access port includes a body member having a proximal end and a distal end, a portion of the body member secured within tissue and a plurality of sensors embedded within the body member, the plurality of sensors configured to measure at least one loading parameter between tissue and the surgical access port.

In some embodiments, the plurality of sensors transmit signals indicative of the at least one loading parameter to a processing unit of a robotic surgical system mechanically connected to the surgical instrument. The transmission of the signals may occur wirelessly or through wires and the transmission may occur continuously in real-time.

Methods for estimating a load at a tip of an end effector of a surgical instrument mounted on a robot arm of a robotic surgical system are also described. A method may include quantifying an access port load of a surgical instrument access port from sensor data received from a sensor located between a tissue of a surgical patient coupled to the surgical instrument access port and a shaft of the surgical instrument in the access port. A determined tip load at the end effector of the surgical instrument may be adjusted based at least in part on the measured access port load.

Signals indicative of the access port load may be transmitted through wires or wirelessly from the first sensor to a processing unit of the robotic surgical system. The transmission of the signals may occur continuously and in real-time. The access port load may be related to at least one of a force or a torque applied at the tip of the end effector of the surgical instrument. A force and/or a torque on the surgical instrument attached to the robot arm of the robotic surgical system may be quantified from sensor data of a second sensor in the robot arm of the robotic surgical system. The quantifications received from the first and second sensors may be combined to compute the estimated load at the tip of the end effector of the surgical instrument. The estimated load at the tip of the end effector of the surgical instrument may be provided in real-time to a haptic feedback interface for communicating haptic feedback to a user.

BRIEF DESCRIPTION OF THE DRAWINGS

Objects and features of the presently-disclosed methods and apparatus will become apparent to those of ordinary skill in the art when descriptions of various embodiments thereof are read with reference to the accompanying drawings, of which.

DETAILED DESCRIPTION

Figure 1:
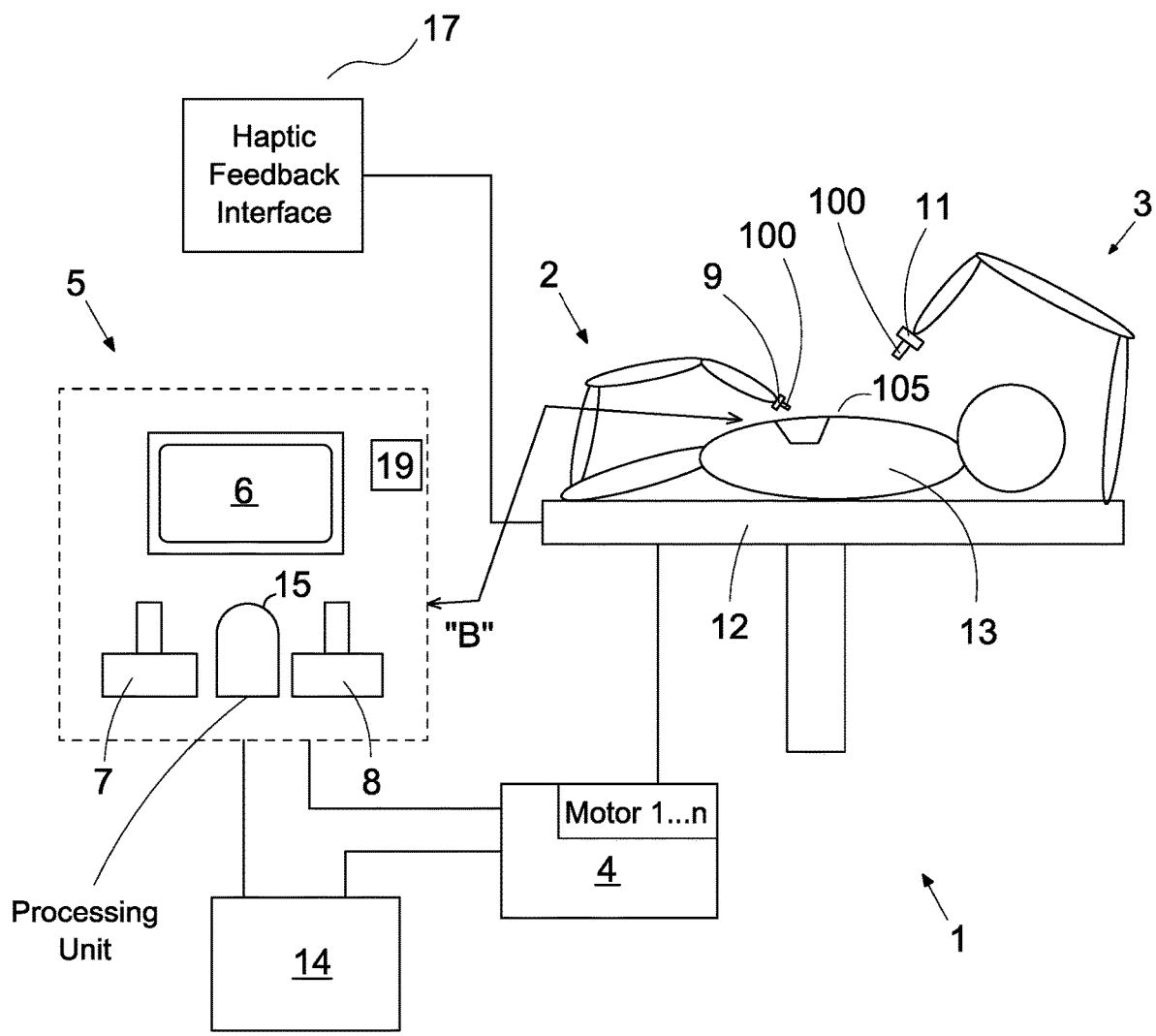
FIG. 1 is a schematic diagram of a robotic surgical system, in accordance with an embodiment of the present disclosure.

A minimally-invasive procedure may be defined as any procedure that is less invasive than open surgery used for the same purpose. As it is used in this description, "endoscopic surgery" is a general term describing a form of minimally-invasive surgery in which access to a body cavity is achieved through several small percutaneous incisions. While endoscopic surgery is a general term, "laparoscopic" and "thoracoscopic" describe endoscopic surgery within the abdomen and thoracic cavity, respectively. Some examples of instruments used in minimally-invasive procedures include graspers, cutters, forceps, dissectors, sealers, dividers, or other tools suitable for use in the area of the anatomical structure of interest.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is farther from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

FIG. 1 is a schematic diagram of a robotic surgical system, in accordance with an embodiment of the present disclosure.

A medical work station is shown generally as work station 1 and generally includes a plurality of robot arms 2, 3, a control device 4, and an operating console 5 coupled with control device 4. Operating console 5 includes a display device 6, which is set up, in particular, to display three-dimensional images, and manual input devices 7, 8, by means of which a person (not shown), for example a surgeon, is able to telemanipulate robot arms 2, 3, in a first operating mode, as known in principle to a person skilled in the art. Display device 6 may receive data or information through wires or in a wireless manner "B" from at least one surgical instrument 100.

Each of robot arms 2, 3, includes a plurality of members, which are connected through joints, and an attaching device 9, 11, to which may be attached, for example, surgical instrument 100 having an end effector, in accordance with any one of several embodiments disclosed herein, as will be described in greater detail below.

Robot arms 2, 3, may be driven by electric drives (not shown) that are connected to control device 4. Control device 4 (e.g., a computer) is set up to activate the drives, in particular by means of a computer program, in such a way that robot arms 2, 3, their attaching devices 9, 11, and thus surgical instrument 100 executes a desired movement according to a movement defined by means of manual input devices 7, 8. Control device 4 may also be set up in such a way that it regulates the movement of robot arms 2, 3, and/or of the drives.

Medical work station 1 is configured for use on a patient 13 lying on a patient table 12 to be treated in a minimally invasive manner by means of surgical instrument 100. At least a portion of surgical instrument 100 is configured to be inserted into tissue of patient 13 via an access port 105. Medical work station 1 may also include more than two robot arms 2, 3, the additional robot arms likewise being connected to control device 4 and being telemanipulatable by means of operating console 5. Medical work station 1 may include a database 14, in particular coupled to with control device 4, in which are stored for example pre-operative data from living being 13 and/or anatomical atlases.

Operating console 5 further includes a processing unit 15. Processing unit 15 may be a controller. The controller can be a, microcontroller, a system on chip (SOC), field programmable gate array (FPGA), etc. The controller may be provided as a single integrated circuit (IC) chip which may be mounted on a single printed circuit board (PCB). Alternatively, the various circuit components of the controller can be provided as one or more integrated circuit chips. That is, the various circuit components are located on one or more integrated circuit chips.

Processing unit 15 may include any type of computing device, computational circuit, or any type of processor or processing circuit capable of executing a series of instructions that are stored in a memory, e.g., storage device and/or external device. In some embodiments, a haptic user interface 17, described below, may be communicatively coupled to processing unit 15. In some embodiments, processing unit 15 may be configured to execute a set of programmed instructions for performing the functionality of control device or controller 4. Processing unit 15 may additionally, or alternatively, be configured to execute a set of programmed instructions for performing a method of controlling endoscopic instruments using a port assembly 105, as disclosed herein.

The haptic feedback may be used in conjunction with the auditory and visual feedback or in lieu thereof to avoid confusion with the operating room equipment which relies on audio and visual feedback. Haptic interface 17 may be an asynchronous motor that vibrates in a pulsating manner. In one embodiment, the vibrations are at a frequency of about 30 Hz or above providing a displacement having an amplitude of 1.5 mm or lower to limit the vibratory effects from reaching a loading unit. It is also envisioned that haptic feedback interface 17 includes different colors and/or intensities of text on screen and/or on switches for further differentiation between the displayed items. The visual, auditory or haptic feedback can be increased or decreased in intensity. For example, the intensity of the feedback may be used to indicate that the forces on the instrument are becoming excessive.

For example, user feedback may be included in the form of pulsed patterns of light, acoustic feedback (e.g., buzzers, bells or beeps that may be sounded at selected time intervals), verbal feedback, and/or haptic vibratory feedback (such as an asynchronous motor or solenoids), for example. The visual, auditory, or haptic feedback can be increased or decreased in intensity. In embodiments, the intensity of the feedback may be used to indicate that the forces on the instrument are becoming excessive.

Figure 2:
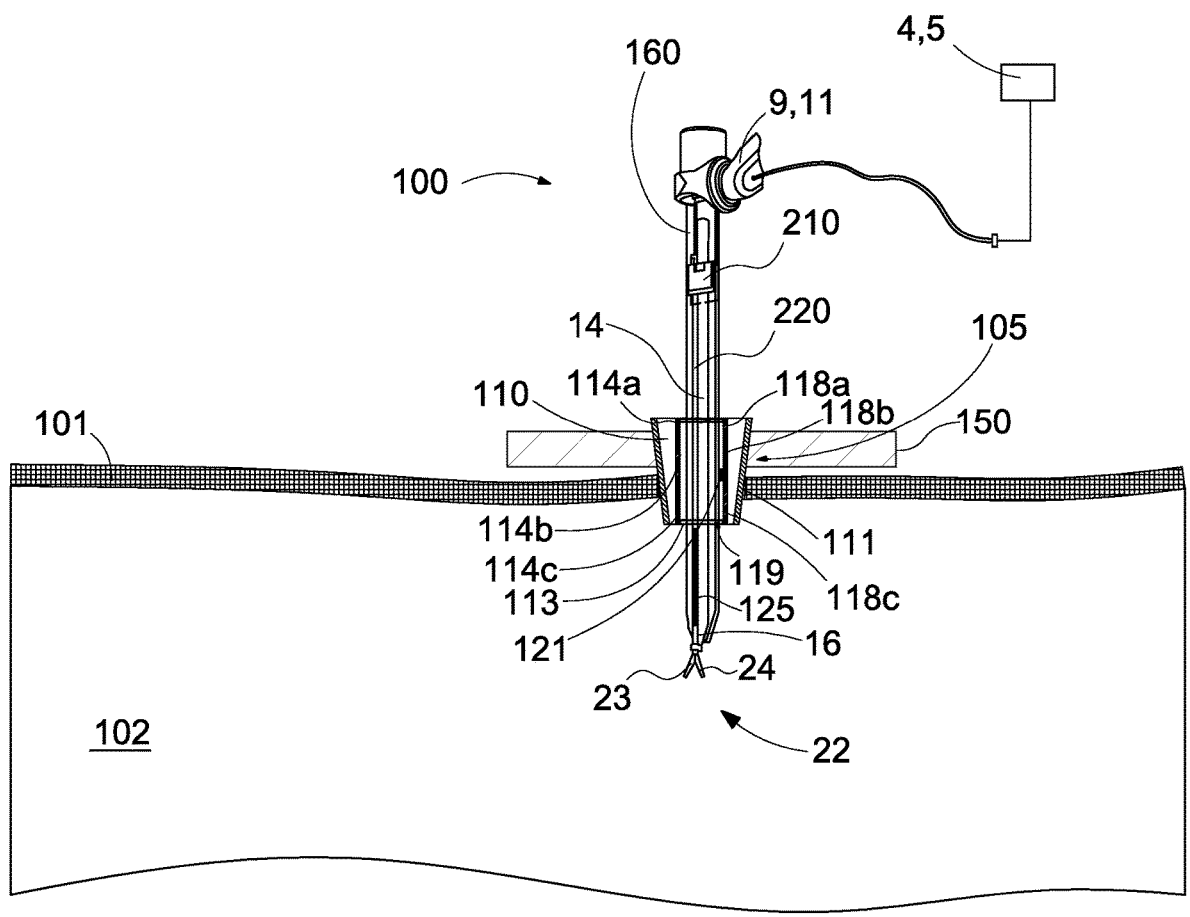
FIG. 2 is a schematic diagram of a surgical instrument inserted through an access port having one or more sensors embedded therein, in accordance with an embodiment of the present disclosure.

FIG. 2 shows surgical instrument 100 inserted through port assembly 105, according to the present disclosure. Port assembly or access port 105 generally includes a body 110. Body 110 of port assembly 105 includes an exterior surface 111, an interior surface 113, and an interior space 119 defined by interior surface 113. Exterior surface 111 of body 110 is shown disposed in sealable contact with tissue 101 at an entry site into the patient's body cavity 102. Body 110 is adapted to allow access into body cavity 102, e.g., to allow access of instruments therethrough, and may include sealing elements or mechanisms to seal the opening into body cavity 102, e.g., to prevent the escape of insufflation gas. Body 110 of port assembly 105 may be formed of any suitable material such as a metal, alloys, composite materials or any combination of such materials.

In some embodiments, port assembly 105 is coupled to a holding member 150. Holding member 150 may be adapted to be attachable to a table or frame to provide support for port assembly 105, e.g., to provide additional stability and/or reduce the weight of the tool on the patient's body. Port assembly 105 may be used with a wide variety of endoscopic instruments or other tools having a shaft suitably configured to be receivable within interior space 119 of port assembly 105.

A plurality of sensors 114a, 114b, 114c, 118a, 118b, and 118c, are coupled to, or otherwise disposed in association with, body 110 of port assembly 105. In some embodiments, the plurality of sensors 114a, 114b, 114c and 118a, 118b, 118c, are pressure sensors. However, one skilled in the art may contemplate using a plurality of different sensors, as will be described below.

In FIG. 2, an embodiment of surgical instrument 100 is shown for use with various surgical procedures and generally includes a housing 210 and a shaft 220 extending distally from housing 210, and an end-effector assembly 22. Shaft 220 has a distal end 16 configured to mechanically engage end-effector assembly 22 and a proximal end 14 configured to mechanically engage housing assembly 210. Surgical instrument 100 may be removably supported on a robotic guide assembly 160. Guide assembly 160 supports surgical instrument 100 in such a manner so as to enable translation of surgical instrument 100 relative to guide assembly 160. Shaft 220 of surgical instrument 100 also includes a sleeve 125 disposed thereon.

End-effector assembly 22 generally includes a pair of opposing jaw assemblies 23 and 24 pivotably mounted with respect to one another. Jaw assemblies 23 and 24 move from an open position, where they are disposed in spaced relation relative to one another, to a clamping or closed position, where jaw assemblies 23 and 24 cooperate to grasp tissue therebetween.

A transmission line operably connects surgical instrument 100 to one of the attaching devices 9, 11. Surgical instrument 100 may alternatively be configured as a wireless device or battery-powered.

In operation, it is desirable to sense forces and torques applied to the tip of surgical instrument 100, such as end effector 22 (e.g., jaws, grasper, blades, etc.) of robotic endoscopic surgical instruments, in order to feed the forces and torques back to the surgeon through the system hand controls or by other means, such as by a visual display or an audible tone. The exemplary embodiments of the present disclosure provide for a system and method of indirectly measuring or estimating forces and torques applied to the tip of surgical instrument 100.

For example, sleeve 125 disposed around shaft 220 of surgical instrument 100 is electrically connected to access port 105 via the plurality of sensors 114a, 114b, 114c, 118a, 118b, 118c. The plurality of sensors 114a, 114b, 114c, 118a, 118b, 118c, measure the forces and torques exerted thereon by surgical instrument 100 at tissue 101, and generate load signal data. The measured load signal data, pertaining to forces and torques, may be sampled and then wirelessly transmitted "B" to processing unit 15 of operating console 5 (see FIG. 1). In accordance with the present disclosure, loads at the tip of surgical instrument 100 are estimated or derived or calculated based on sensor data/information collected by the plurality of sensors 114a, 114b, 114c, 118a, 118b, 118c, embedded or incorporated within access port 105. In this manner, sensors need not be placed at any distal portions of surgical instrument 100.

Figure 4:
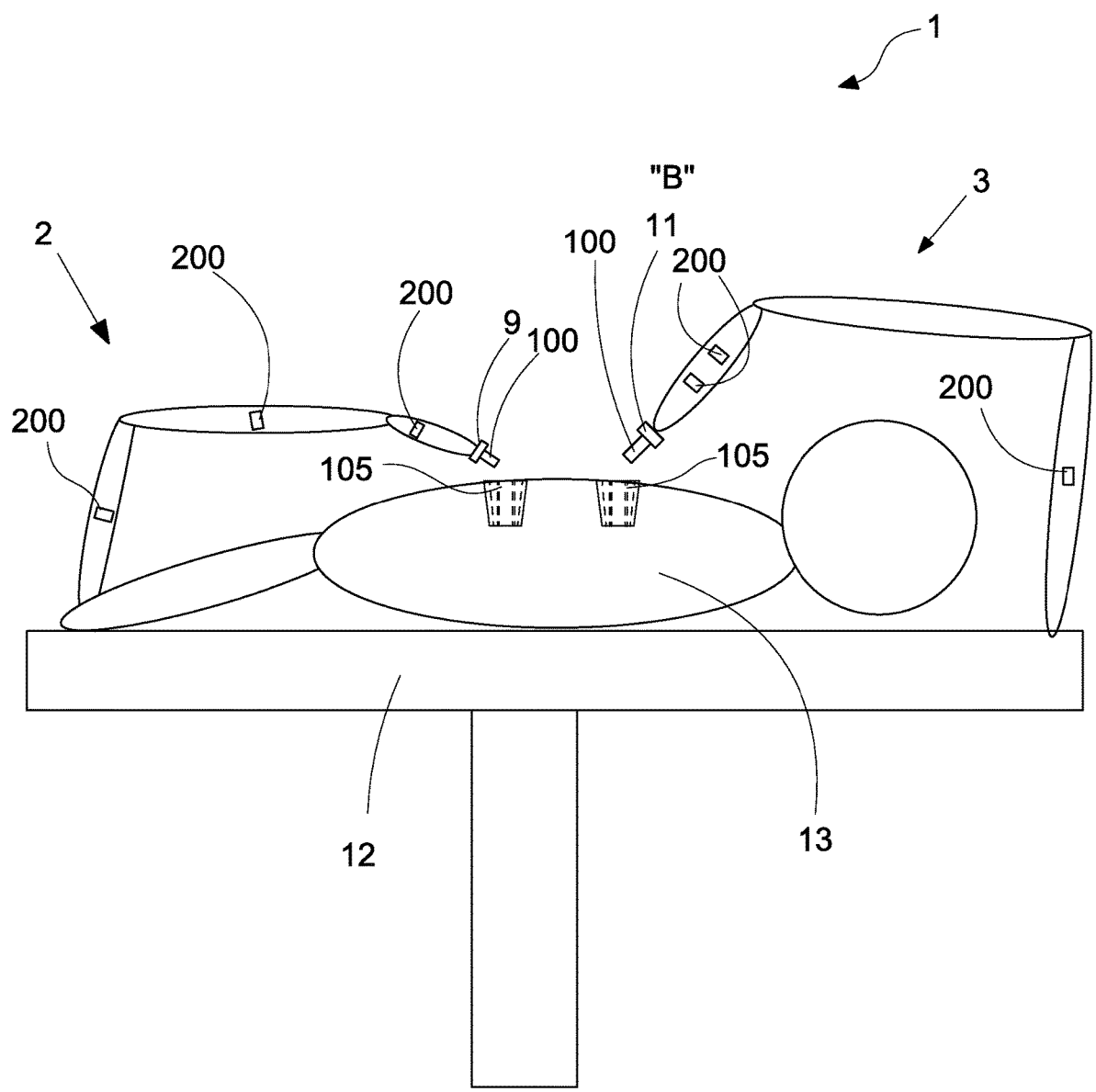
FIG. 4 is a schematic diagram illustrating the surgical instrument approaching an access port having one or more sensors embedded therein, the surgical instrument attached to a robot arm of the robotic surgical system, in accordance with another embodiment of the present disclosure.

Moreover, the load signal data or other information collected by the plurality of sensors 114a, 114b, 114c, 118a, 118b, 118c, may be combined with additional sensor data. For example, as shown in FIG. 4, robot arms 2, 3, and attaching devices 9, 11, may include a plurality of sensors 200. FIG. 4 provides a schematic diagram illustrating surgical instrument 100 approaching access port 105 having one or more sensors embedded therein. Sensors 200 monitor and measure forces and torques on attaching devices 9, 11, of robot arms 2, 3, of the robotic surgical system. The plurality of sensors 200 measure forces and torques passing through surgical instrument 100 at the location where it is mounted to attaching devices 9, 11; measure forces and torques on any motor drive mechanisms passing from the attaching devices 9, 11, to surgical instrument 100; and measure the forces and torques between surgical instrument 100 and access port 105 when end effector 22 passes through tissue 101 toward body cavity 102.

The sensor information collected from the plurality of sensors 114a, 114b, 114c, 118a, 118b, 118c, embedded or incorporated within access port 105, are combined with sensor information collected from the plurality of sensors 200, mounted on attaching devices 9, 11, and robot arms 2, 3, in order to estimate loads (e.g., forces and torques) at the tip of surgical instrument 100, without the need to place sensors directly on any distal portion of the surgical instrument itself.

Therefore, the measurements of the forces and torques at the distal end (or tip) of surgical instrument 100 are derived from data or information collected from the plurality of sensors 114a, 114b, 114c, 118a, 118b, 118c, embedded or incorporated within or on access port 105 and the plurality of sensors 200 embedded on the robotic surgical system. The plurality of sensors 114a, 114b, 114c, 118a, 118b, 118c, embedded or incorporated within or on access port 105 continuously send, in real-time, the state of the loading between sleeve 125 of shaft 220 of surgical instrument 100 to processing unit 15 of the robotic surgical system. Such information is then combined with the state of the loading of surgical instrument 100 at attaching devices 9, 11, to the robotic surgical system, which is received by processing unit 15, in order to estimate (at a constant rate) the surgical instrument loads. This combined information may then be provided to haptic user interface 17 (see FIG. 1) to allow a user to continuously adjust the drive information and/or power information of surgical instrument 100.

Figure 3A:
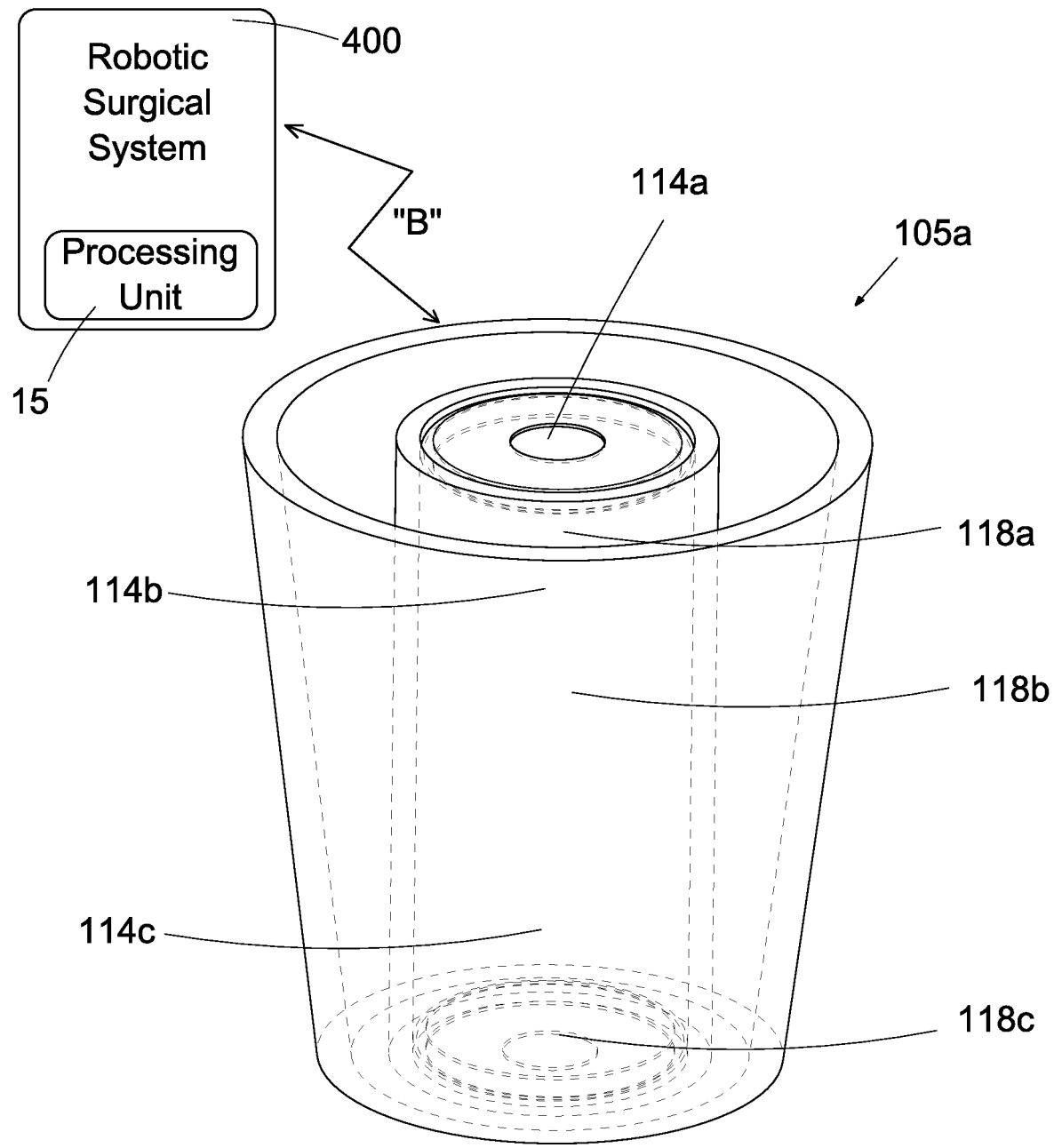
FIG. 3A is a schematic diagram of an access port having a plurality of sensors incorporated on the inner surface of the access port, and communicating with a processing unit of the robotic surgical system, in accordance with an embodiment of the present disclosure.
Figure 3B:
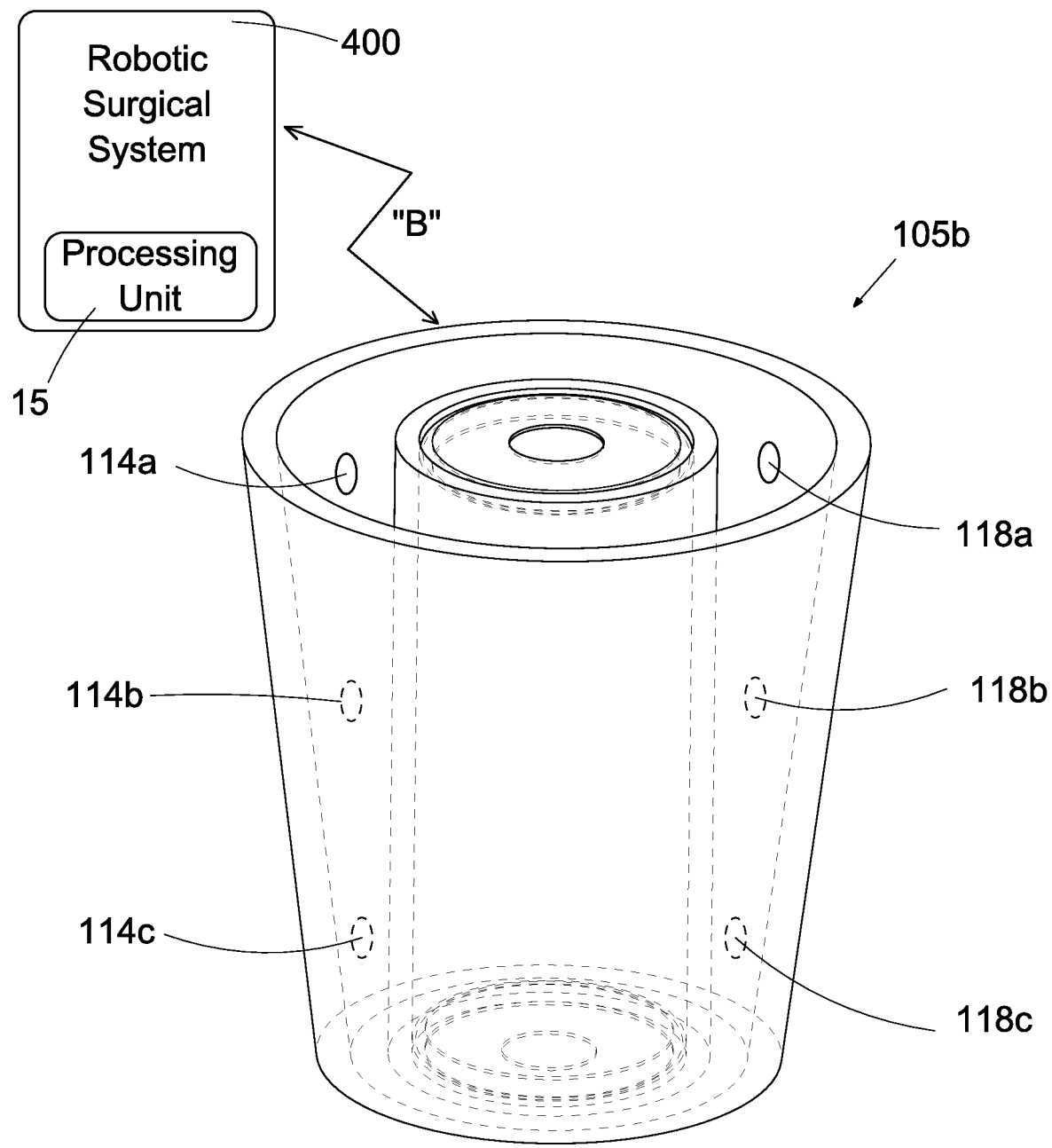
FIG. 3B is a schematic diagram of an access port having a plurality of sensors incorporated within the walls of the access port, and communicating with a processing unit of the robotic surgical system, in accordance with an embodiment of the present disclosure.

FIG. 3A is a schematic diagram of an access port 105a having a plurality of sensors incorporated on the inner surface thereof, and wirelessly communicating with processing unit 15 of robotic surgical system 400, in accordance with an embodiment of the present disclosure, whereas FIG. 3B is a schematic diagram of an access port 105b having a plurality of sensors incorporated within the walls thereof, and wirelessly communicating with processing unit 15 of robotic surgical system 400, in accordance with another embodiment of the present disclosure.

With reference to FIGS. 3A and 3B, the plurality of sensors 114a, 114b, 114c, 118a, 118b, 118c, are circumferentially placed, in an equally spaced apart manner, on access port 105. The plurality of sensors 114a, 114b, 114c, 118a, 118b, 118c, detect the presence of surgical instrument 100 or other object within the working channel or space 119 of body 110 of access port 105 (see FIG. 2).

The plurality of sensors 114a, 114b, 114c, 118a, 118b, 118c, may be selected from a wide array of sensor types. For example, the plurality of sensors 114a, 114b, 114c, 118a, 118b, 118c, may be optical, mechanical, electromagnetic or thermal sensors. The plurality of sensors 114a, 114b, 114c, 118a, 118b, 118c, may also be proximity sensors for detecting the presence of nearby objects. The plurality of sensors 114a, 114b, 114c, 118a, 118b, 118c, can be of different types, sizes, and/or tolerances depending on whether they are used for detecting the presence of surgical instruments.

The outputs of the plurality of sensors 114a, 114b, 114c, 118a, 118b, 118c, may be electrically coupled or otherwise electrically communicated to control circuitry (e.g., processing unit 15). The output signals of the plurality of sensors 114a, 114b, 114c, 118a, 118b, 118c, may also be transmitted through wires or wirelessly to processing unit 15 (see FIGS. 3A and 3B).

Wireless transmitter 121 (see FIG. 2) is configured to wirelessly transmit, or broadcast the processed signal to wireless receiver 19 (see FIG. 1). As mentioned above, in some embodiments, the signal is analog, or converted to analog, and modulated with a carrier frequency, 2.4 GHz, by processing unit 15. Accordingly, wireless transmitter 121 may be configured to broadcast the modulated analog signal to wireless receiver 19. In other embodiments, where the signal is digital, or digitized, and modulated by the processing component, wireless transmitter 121 may be configured according to a standard protocol, e.g., Bluetooth®. Alternatively, any other suitable configuration of hardwired or wireless transmitter, standard or proprietary, may be used. Further, wireless transmitter 121 may include an antenna (not shown) extending therefrom to facilitate transmission of the signal to wireless receiver 19. The antenna (not shown) may be configured as a low profile antenna protruding minimally from housing 110 of access port 105, or may be internally disposed within housing 110 of access port 105.

Wireless transmitter 121 is configured to transmit the signal wirelessly to wireless receiver 19. It is envisioned that wireless receiver 19 also includes an antenna (not shown) to facilitate reception of the signal from wireless transmitter 121. It is further envisioned that wireless transmitter 121 and wireless receiver 19 have a working range suitable for use in an operating room or other surgical setting. In other words, it is envisioned that wireless transmitter 121 may be capable of communication with wireless receiver 19 throughout the entire surgical procedure. Wireless receiver 19 is configured to decouple, or demodulate, the signal and communicate the signal to video monitor 6 (see FIG. 1). Wireless receiver 19 may include standard electrical connections, such that wireless receiver 19 may be coupled to video monitor 6. Video monitor 6 may display the signal as a video image.

Systems and methods in accordance with the present disclosure employ a smart access port having a plurality of sensors embedded or incorporated therein. The smart access port communicates with one or more surgical instruments attached to robot arms of a robotic surgical system. Loads (e.g., forces and torques) sensed by the plurality of sensors of the smart access port, as well as loads (e.g., forces and torques) sensed by attaching devices and robot arms of the robotic surgical system are combined in order to estimate or calculate or approximate loads at the tip or end effector of the one or more surgical instruments attached to the robot arms of the robotic surgical system. Therefore, the distal ends or end effectors or shaft portions of the one or more surgical instruments are devoid of any sensors incorporated thereon, thus reducing the cost and complexity of manufacturing such surgical instruments.

Moreover, in embodiments, the plurality of sensors may provide for an independent measure of the loads between the surgical instrument(s) and the abdominal wall. This serves as an independent safety system monitoring that the robotic surgical system does not present excessive loads to the abdominal wall. If these loads exceed a predetermined threshold, the robot safety system can, for example, power down the robotic surgical system.

In embodiments, the robotic surgical system includes one or more feedback devices. The one or more feedback devices may provide any suitable form of sensory feedback, such as, for example, auditory feedback (sound), haptic or tactile feedback (touch), optical feedback (visual), olfactory feedback (smell), and/or equilibrioception (balance feedback). Haptic feedback may be provided through various forms, for example, mechanosensation, including, but not limited to, vibrosensation (vibrations) and pressure-sensation, thermoperception (heat), and/or cryoperception (cold). It will be appreciated by those skilled in the art that any single feedback type, or any combination thereof, may be used to provide a user with feedback from the robotic surgical system. In some embodiments, properties of the feedback may provide a quantitative indication of the predetermined conditions. For example, a quantitative indication of a temperature of the end effector may be provided by an audio tone having a pitch that varies with temperature, a series of pulses having a pulse frequency that varies with temperature, etc.

The devices disclosed herein can be designed to be disposed of after a single use, or can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A method of estimating a load at a tip of an end effector of a surgical instrument mounted on a robot arm of a robotic surgical system, the method comprising:
   quantifying an access port load of a surgical instrument access port from sensor data received from a sensor located between a tissue of a surgical patient, in contact with the surgical instrument access port, and a shaft of the surgical instrument in the access port, wherein the access port load is related to at least one of a force or a torque applied at the tip of the end effector of the surgical instrument;
   adjusting a determined tip load, at the end effector of the surgical instrument, based at least in part on the measured access port load; and
   quantifying at least one of a force or a torque on the surgical instrument attached to the robot arm of the robotic surgical system from sensor data of a second sensor in the robot arm of the robotic surgical system, wherein quantifications received from the first and second sensors are combined to compute an estimated load at the tip of the end effector of the surgical instrument.

2. The method according to claim 1, further comprising wirelessly transmitting signals indicative of the access port load from the first sensor to a processing unit of the robotic surgical system.

3. The method according to claim 2, wherein wireless transmission of the signals occurs continuously and in real-time.

4. The method according to claim 1, wherein the estimated load at the tip of the end effector of the surgical instrument is provided in real-time to a haptic feedback interface for communicating haptic feedback to a user.

5. The method according to claim 4, wherein the haptic feedback increases or decreases in intensity in response to a specific event, occurrence, or operational characteristic related to the estimated load.

6. The method according to claim 1, further comprising detecting a presence of the shaft of the surgical instrument in the access port.

7. A method of estimating a load at a tip of an end effector of a surgical instrument mounted on a robot arm of a robotic surgical system, the method comprising:
   quantifying an access port load of a surgical instrument access port, secured within tissue of a patient, from sensor data received from a plurality of sensors embedded within a body member of the access port, the plurality of sensors configured to measure at least one loading parameter exerted thereon by the access port when in contact with the tissue, wherein the plurality of sensors include:
   a distal sensor located proximate the distal end of the body member;
   a proximal sensor located proximate the proximal end of the body member; and
   an intermediate sensor located between the distal sensor and the proximal sensor, wherein the access port load is related to at least one of a force or a torque applied at the tip of the end effector of the surgical instrument;
   adjusting a determined tip load, at the end effector of the surgical instrument, based at least in part on the measured access port load; and
   quantifying at least one of a force or a torque on the surgical instrument attached to the robot arm of the robotic surgical system from sensor data of a sensor located in the robot arm of the robotic surgical system, wherein quantifications received from the plurality of sensors and the sensor located in the robot arm are combined to compute an estimated load at the tip of the end effector of the surgical instrument.

8. The method according to claim 7, further comprising wirelessly transmitting signals indicative of the access port load from the plurality of sensors to a processing unit of the robotic surgical system.

9. The method according to claim 8, wherein wireless transmission of the signals occurs continuously and in real-time.

10. The method according to claim 7, further comprising securing the access port in the tissue of the patent such that at least the distal sensor of the plurality of sensors is disposed within a body cavity of a patient.

11. The method according to claim 10, further comprising securing the access port in the tissue of the patient such that at least the proximal sensor of the plurality of sensors is disposed external of the body cavity of the patient.

12. The method according to claim 7, wherein the estimated load at the tip of the end effector of the surgical instrument is provided in real-time to a haptic feedback interface for communicating haptic feedback to a user.

13. The method according to claim 12, wherein the haptic feedback increases or decreases in intensity in response to a specific event, occurrence, or operational characteristic related to the estimated load.

14. The method according to claim 7, further comprising detecting a presence of a shaft of the surgical instrument in the access port.

* * * * *